United States Patent [19]

Hovis

[11] Patent Number: 5,209,907
[45] Date of Patent: May 11, 1993

[54] FLUID FLOW CONTROL AND ISOLATION
[75] Inventor: Keith W. Hovis, Bartlesville, Okla.
[73] Assignee: Phillips Petroleum Company, Bartlesville, Okla.
[21] Appl. No.: 894,370
[22] Filed: Jun. 4, 1992

Related U.S. Application Data
[62] Division of Ser. No. 632,819, Dec. 24, 1990.
[51] Int. Cl.[5] .............................................. F28D 21/00
[52] U.S. Cl. .................................... 422/208; 422/214; 422/228; 422/234; 422/235; 422/256; 422/295; 585/705; 210/539; 210/540
[58] Field of Search ............... 422/206, 208, 224, 228, 422/234, 235, 255-256, 198, 295; 55/171; 210/539, 540; 585/705

[56] References Cited
U.S. PATENT DOCUMENTS

| | | | |
|---|---|---|---|
| 4,249,030 | 2/1981 | Chapman et al. | 422/235 |
| 4,532,034 | 7/1985 | Hans et al. | 210/539 |
| 4,608,160 | 8/1986 | Zoch | 210/540 |
| 4,747,947 | 5/1988 | Bannon | 210/539 |

Primary Examiner—Robert J. Warden
Assistant Examiner—Krisanne M. Thornton
Attorney, Agent, or Firm—Charles W. Stewart

[57] ABSTRACT

An improved system for performing an alkylation process and a method for handling liquid catalyst in an alkylation process. This improvement involves a method and apparatus by which liquid alkylation catalyst contained in alkylation process equipment can be safely stored and isolated from the external environment. Additionally, the apparatus improvement will allow for an improved method for controlling the circulation of liquid alkylation catalyst by providing means for quickly stopping the circulation of alkylation catalyst. The apparatus improvement includes a baffle contained within a vessel which is attached to the bottom of the vessel and extends upwardly into the vessel. The baffle is designed to allow for the liquid flow between the inside of the vessel and the inside of the baffle and it allows for the venting into a vapor space from the top of the baffle. Within the baffle is standpipe which provides for fluid flow from within the baffle to a region outside the vessel.

3 Claims, 2 Drawing Sheets

FLUID FLOW CONTROL AND ISOLATION

This is a divisional of application Ser. No. 07/632,819, filed Dec. 24, 1990, now allowed.

This invention relates to a method and apparatus for handling fluids.

A common process used in the petroleum refining industry is an alkylation process where high octane gasoline is produced by reacting, in the presence of catalyst, preferably hydrogen fluoride, isoparaffins with olefin compounds. One commonly used version of this alkylation process is similar to that disclosed in U.S. Pat. No. 3,213,157 which uses a settling vessel, reactor riser, and a cooler heat exchanger that are combined in a manner which allow for the natural circulation of liquid alkylation catalyst. A hydrocarbon feed mixture of isoparaffins and olefins is introduced into the inlet of a reactor riser at which point cooled alkylation catalyst exiting from a heat exchanger is intimately mixed with the hydrocarbon feed thereby forming a hydrocarbon-catalyst mixture. Due to the density difference between the hydrocarbon-catalyst mixture and catalyst, the mixture flows upwardly by natural convection through the riser-reactor with the reactor effluent ultimately discharging into a settler vessel. In the settler vessel, separation of the non-miscible hydrocarbon phase from the catalyst phase takes place with the catalyst phase settling to the lower portion of the vessel to form a liquid-liquid interface between the hydrocarbon and catalyst. The settled-out catalyst returns by gravity to the heat exchanger located somewhere below the settler where it is cooled and again mixed with incoming hydrocarbon feed to repeat the cycle. The operating conditions of such an alkylation process are well known in the art and have been disclosed in many various publications and, for example, in U.S. Pat. No. 3,213,157, No. 3,249,650, and No. 3,544,651.

A concern associated with the operation of alkylation processes is the safe handling, transportation, and storage of alkylation catalyst. It is common for as much as 60 percent of the total alkylation catalyst inventory used in an alkylation process to be contained within the settler vessel. In many instances, the alkylation catalyst being used in the process can be a dangerous compound and, consequently, it becomes important to minimize any potential for leakage of this catalyst into the atmosphere. Because of the safety considerations associated with the catalyst handling, it is important that a quick and efficient method and apparatus be developed so as to allow the quick and efficient isolation of alkylation catalyst in the event of catalyst leaks into the atmosphere.

Accordingly, an object of this invention is to provide method and apparatus for the quick and efficient isolation of alkylation catalyst within a vessel.

In one embodiment of this invention, a vessel is provided with a baffle means which is fixedly attached to the bottom of said vessel and extends upwardly to within close proximity of the top end of said vessel. The baffle means is provided with conduit means placed near the bottom of the baffle means and venting means at the top end of said baffle means. A standpipe conduit means is provided within the baffle means with a first end placed at a pre-selected position within the baffle means and extending generally vertically through the bottom of said vessel with the second end of the standpipe conduit means terminating at a point exterior to said vessel. With this invention, the circulation of a liquid catalyst being used in an alkylation process can be quickly and safely stopped and the liquid alkylation catalyst can be safely isolated from the environment external to said vessel.

BRIEF DESCRIPTION OF THE DRAWINGS

Other objects, advantages and features of this invention will become apparent from a study of this disclosure, appended claims and drawings in which:

Referring now to FIG. 1, there is illustrated a vessel 10, which defines a volume comprising a top zone 11, a medial zone 12, and a bottom zone 13, having an inlet nozzle 14 and outlet nozzles 15, 16, and 18. Vessel 10 can be any suitable type of vessel including, but not limited to, spherically shaped vessels, horizontally shaped vessels and vertically shaped vessels which is capable of receiving and holding liquids or mixtures of two or more liquids. Preferably, vessel 10 is to be a vertical vessel with any suitable type of end-heads which can include hemispherically shaped heads, elliptically shaped heads and conically shaped heads. Generally, the end-heads of a vertical vessel are elliptical in shape.

Figure 3:
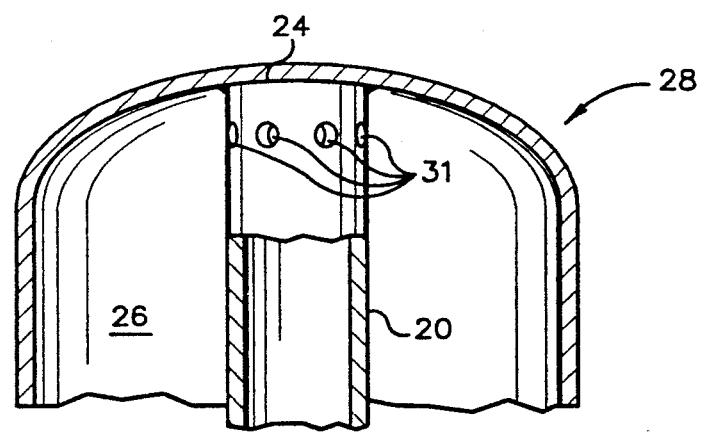
FIG. 3 is an elevational view in cross-section of a different venting means from that shown in FIG. 1 which can be another embodiment of the inventive apparatus.

Disposed within vessel 10 is a baffle 20, which defines a space and provides means for segregating and directing fluid flow. Baffle 20 is preferably, but not necessarily, cylindrical in shape and has a first end 22 and a second end 24. First end 22 of baffle 20 is fixedly secured in place and is supported at the bottom of vessel 20. The first end 22 of baffle 20 is fixedly secured in place by any suitable method or means known in the art which can include welding or any other suitable means for attachment. Baffle 20 extends upwardly from the bottom end of vessel 20 into top zone 11 of vessel 10. In one embodiment of the invention, second end 24 of baffle 20 terminates in top zone 11 of vessel 10 at a position within close proximity of top end 25 of vessel 10. Second end 24 remains open to top zone 11 thereby providing vent 28 which provides means for fluid flow communication between top zone 11 and space 30 defined by baffle 20. As an alternative embodiment of this invention, second end 24 of baffle 20 can extend to within close proximity of, or in contact with, the inside surface of top end 25 of vessel 10 at which position it is affixed by any suitable means, such as by welding, as illustrated in FIG. 3. Vent 28 can be any suitable design which permits fluid flow communication between top zone 11 and space 30 and, as is illustrated in FIG. 3, one embodiment preferably uses a series of apertures 31 which pass through the wall of baffle 20.

Passing through the wall of bottom end 33 of vessel 10 is standpipe conduit 32 having a first end 34 positioned at a preselected intermediate location within space 30 and second end 36 at a position external and below vessel 10. Conduit 32 provides means for conveying fluid from vessel 10 to the exterior of vessel 10.

Outlet nozzle 15 is operably connected to and is in communication with standpipe conduit 32.

Conduit 38 provides means for fluid flow communication between outlet nozzle 15 and inlet 39 of catalyst cooler 40. Catalyst cooler 40 provides means for exchanging heat energy between fluids and for removing heat energy, which is primarily generated by exothermic alkylation reactions, from the circulating liquid catalyst phase. Any suitable means for exchanging heat can be used. Examples of such heat exchange means are illustrated and described in *Perry's Chemical Engineers' Handbook, Sixth Edition*, edited by D. W. Green (McGraw-Hill, 1984) at pp 11-1 through 11-30. It is preferred to use conventional shell-and-tube type heat exchangers with cooling water as the cooling medium.

In fluid flow communication with outlet 41 of catalyst cooler 40 and inlet nozzle 14 is riser-reactor 42 having a lower portion and an upper portion. Riser-reactor 42 defines a reaction zone and provides means for conveying fluid from catalyst cooler 40 to vessel 10. Within riser-reactor 42 a mixture comprising a catalyst and a hydrocarbon feed material comprising olefin compounds, isoparaffin compounds and normal paraffins is reacted to produce an alkylate product. Hydrocarbon feed material comprising a mixture of olefins and isoparaffins is introduced through conduit 44 into the lower portion of riser-reactor 42. As the hydrocarbon feed material is introduced, circulating liquid catalyst flows by natural circulation from vessel 10 via standpipe conduit 32 and conduit 38 through catalyst cooler 40 and mixes with the hydrocarbon feed material introduced via conduit 44 to form an admixture. A presently preferred liquid catalyst for use in the system of the present invention comprises a mixture of HF acid and water.

The formed admixture rises upwardly through riser-reactor 42 where the effluent from riser-reactor 42 discharges into vessel 10 via inlet nozzle 12. Upon entering vessel 10, two separate liquid phases form, with the heavier catalyst phase 46 settling to bottom zone 13 of vessel 10 and with the lighter hydrocarbon phase 48 forming in medial zone 14 of vessel 10 above catalyst phase 46 to form liquid-liquid interface 50 therebetween. The catalyst circulates continuously through the system by settling out in vessel 10 and passing through standpipe conduit 32, conduit 38, catalyst cooler 40, riser-reactor 42, and through inlet nozzle 14 thus discharging into vessel 10.

Also included as a part of vessel 10 are outlet nozzles 16 and 18 that are positioned in a spaced relationship and so as to be in fluid flow communication with medial zone 12 of vessel 10. Outlet nozzles 16 and 18 provide means for withdrawing hydrocarbon 48 from vessel 10. Outlet nozzle 16 is operably attached to and is in fluid flow communication with conduit 52 providing means for fluid flow communication between outlet nozzle 16 and surge vessel 54. Outlet nozzle 18 is operably attached to and is in fluid flow communication with conduit 56 that is in fluid flow communication between outlet nozzle 18 and conduit 56 that is in fluid flow communication between outlet nozzle 18 and conduit 52. Interposed in conduit 56 is valve 58, which is normally in the closed position, but alternatively, can be in the open position, for controlling the level of hydrocarbon 48 in vessel 10. Surge vessel 54 is generally placed at an elevation below that of vessel 10 so as to allow for the gravity flow of hydrocarbon 48 from vessel 10 to surge vessel 54. In fluid flow communication with the suction inlet of pump 60 is surge vessel 54. Pump 60 provides means for imparting energy head to the hydrocarbon, which flows into surge vessel 54 by gravitational motive force, and for conveying the hydrocarbon product downstream for further processing (not shown). Any suitable pumping means can be used for pump 60, and examples of such pumping means are illustrated and described at length in *Perry's Chemical Engineers' Handbook, Sixth Edition*, edited by D. W. Green (McGraw-Hill, 1984) at pp 6-6 through 6-17. It is preferred that pump 60 be a centrifugal pump.

The apparatus and method of this invention are designed to provide a safe, quick, reliable and efficient manner in which to isolate a large volume of alkylation catalyst in the rare event that a leak may occur in some of the appurtenant equipment to an alkylation settler vessel such as vessel 10. An admixture comprising hydrocarbon alkylate, hydrocarbon and alkylation catalyst is discharged into vessel 10 from riser-reactor 42 through inlet nozzle 14. Upon entering vessel 10, due to the immiscibility of the hydrocarbons and alkylation catalyst, two liquid phases quickly form with the heavier catalyst phase falling to bottom zone 13 of vessel 10 and the lighter hydrocarbon phase forming above the catalyst phase in medial zone 12 of vessel 10. Because vessel 10 is not operated in a liquid full manner, an additional vapor phase is formed above the hydrocarbon phase in top zone 11 of vessel 10 thus creating three zones within the vessel volume defined by the walls of vessel 10. These zones can be defined as top zone 11 comprising vapor space 26 of the vessel 10, medial zone 12 comprising hydrocarbon phase 48 contained within vessel 10, and bottom zone 13 comprising catalyst phase 46 contained within vessel 10.

Figure 1:
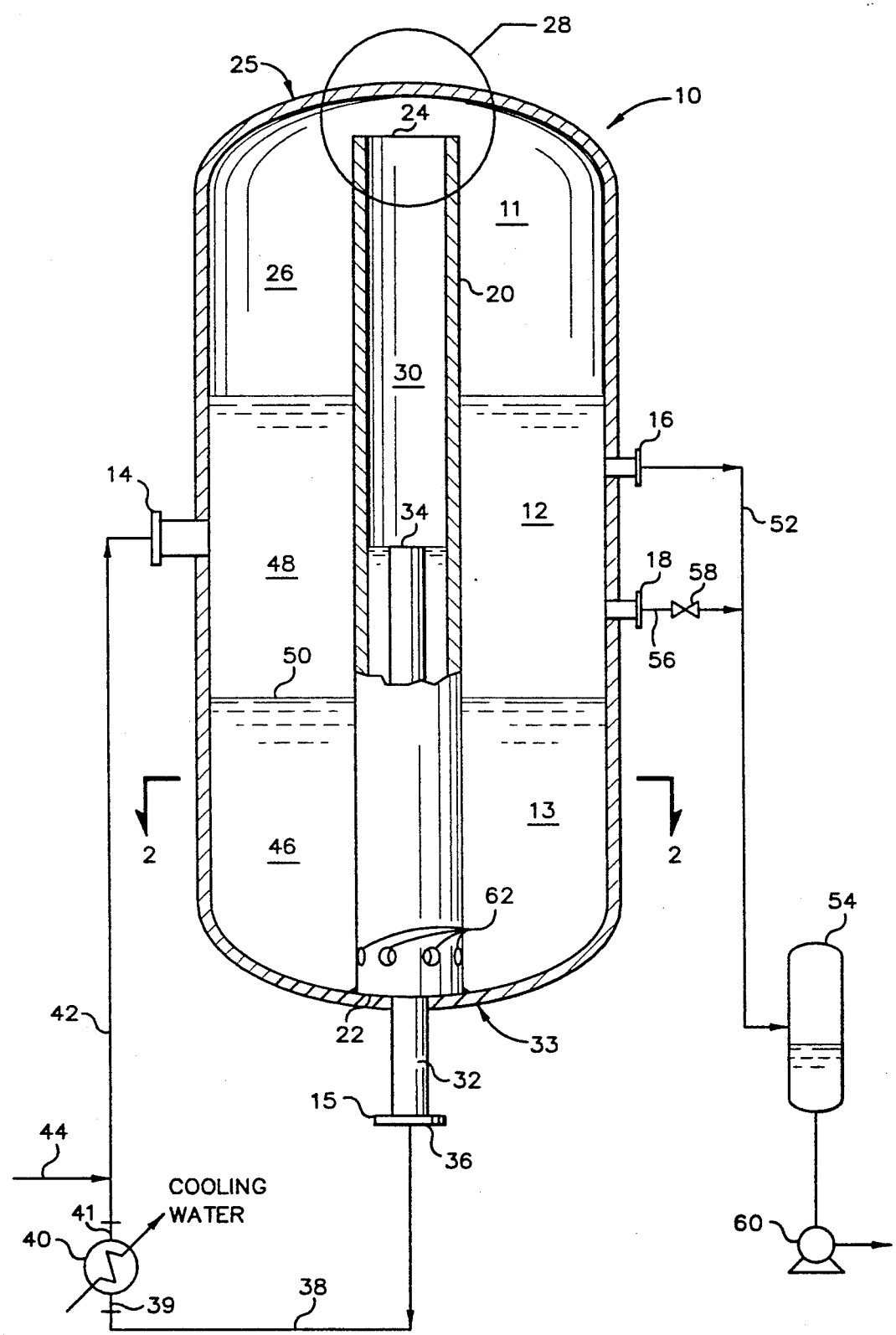
FIG. 1 is an elevational view in cross-section of one embodiment of the inventive apparatus along with a simplified schematic representation of the process flows associated with the inventive apparatus.
Figure 2:
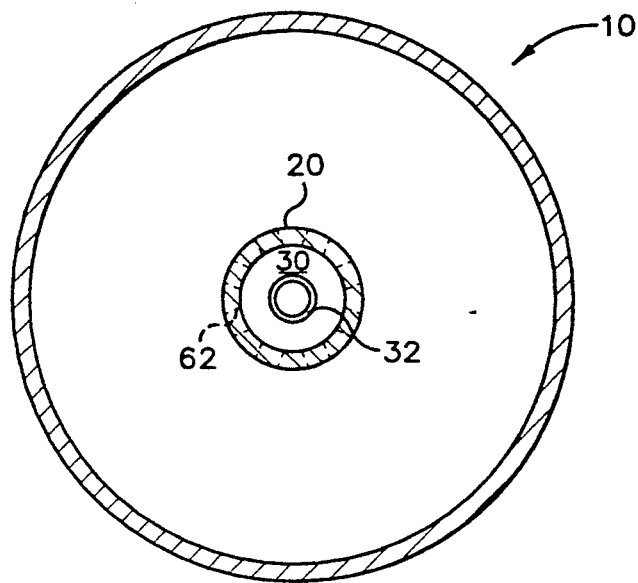
FIG. 2 is a cross-sectional view taken along line 2—2 of FIG. 1.

In the operation of vessel 10, hydrocarbon phase 48 should be maintained at a sufficient elevation level above interface 50 so as to create enough hydrostatic pressure head to drive catalyst phase 46 through conduits 62 of baffle 20 and so as to maintain a catalyst level within space 30 to at least the height of first end 34 of standpipe conduit 32. Conduits 62 are generally placed near bottom end 33 of vessel 10 and is proximately located near first end 22 of baffle 20. Any suitable means can be used as conduits 62 which provides for fluid flow communication between space 30 and the remaining inside vessel 10 defined by the inside walls of vessel 10. As shown in FIG. 1, conduits 62 comprise a group of apertures passing through the inside and outside walls of baffle 20 and are placed in close relationship with first end 22 of baffle 20. The height of the catalyst phase within space 30 of baffle 20 above interface 50 is essentially set by the balancing of the height of the catalyst phase within space 30 that is above interface 50 against the height of the hydrocarbon phase 48 that is above interface 50.

The following Equation 1 is presented to further illustrate the balancing of the hereinabove described elevation heads.

$$(Y_{hc} - Y_a)\rho_{hc} = (Y_i - Y_a)\rho_a \qquad \text{Equation 1}$$

Where:

$Y_{hc}$ is the elevation of hydrocarbon phase 48
$Y_a$ is the elevation of catalyst phase 46
$Y_i$ is the elevation of the catalyst phase within space 30
$\rho_{hc}$ is the density of the hydrocarbon phase
$\rho_a$ is the density of the catalyst phase.

Solving Equation 1 for $Y_i$ gives the following formula for determining the elevation of the catalyst phase within space 30:

$$Y_i = (Y_{hc} - Y_a)\frac{\rho_{hc}}{\rho_a} + Y_a \qquad \text{Equation 2}$$

Equations 1 and 2 above ignore the affect of the density of the vapor phase 26 of top zone 11 above the liquid phases within vessel 10 because the density of the vapor phase is relatively low as compared with the densities of the acid phase and the hydrocarbon phase thus having a negligible impact on the overall hydrostatic heads.

As can be seen from the above Equation 2, as hydrocarbon phase 48 level ($Y_{hc}$) is raised, the level of the catalyst phase within space 30 ($Y_i$) is also raised; and, alternatively, as hydrocarbon phase 48 level ($Y_{hc}$) is lowered, the catalyst phase within space 30 ($Y_i$) is also lowered. Therefore, the level of the catalyst phase within space 30 can be conveniently controlled by controlling the level of hydrocarbon phase 48; however, the maximum height of the catalyst phase within space 30 ($Y_i$) is set by the position of first end 34 through which the catalyst phase flows to enter standpipe conduit 32. Hydrocarbon phase 48 level ($Y_{hc}$) is controlled by the rate of withdrawal of hydrocarbon product via conduits 52 and 56 relative to the rate of input of hydrocarbon feed via conduit 44. Generally, if the withdrawal rate of hydrocarbon product is relatively greater than the hydrocarbon feed input, hydrocarbon phase 48 level ($Y_{hc}$) will fall thereby lowering the available elevation head for driving the acid phase up into space 30. If the hydrocarbon phase 48 level ($Y_{hc}$) falls significantly enough, the level of catalyst phase within space 30 ($Y_i$) will fall below first end 34 of standpipe conduit 32 resulting in the cessation of acid phase circulation through standpipe conduit 32 and the circulation circuit further comprising conduit 38, catalyst cooler 40, and riser-reactor 42.

During the normal operation of the apparatus, it is preferred that hydrocarbon level 48 be sufficiently above interface 50 to give the desired catalyst circulation through the circulation circuit. In the event that there is a leak of catalyst in equipment external to vessel 10, for instance, somewhere within the above described circulation circuit, the apparatus of this invention provides for a method that will allow the immediate cessation of the catalyst circulation through the circulation circuit and the isolation of a large volume of the catalyst inventory within vessel 10. This cessation and isolation of the catalyst is achieved by withdrawing hydrocarbon from hydrocarbon phase 48 through conduit 52 or, alternatively, through conduit 56, or both, at a rate that will lower the elevation of hydrocarbon phase 48 such that the catalyst level within space 30 is lowered below first end 34 of standpipe conduit 32. Once the catalyst level is lowered below first end 34, catalyst circulation will immediately cease and the catalyst contained within vessel 10 will be isolated from the external environment.

Reasonable variations and modifications can be made in the combination and arrangement of parts or elements or in the processes as heretofore set forth in the specification and as shown in the drawings without departing from the spirit and scope of the invention as defined in the following claims.

That which is claimed is:

1. A method for separating an admixture of two immiscible fluids having different densities, comprising the steps of:
   providing a vessel defining a volume comprising a top zone, a medial zone and a bottom zone, said vessel having (1) an inlet means for accepting said admixture into said volume, said volume sufficient to allow said admixture to separate, and (2) an outlet means in said medial zone for withdrawing a separated liquid having lesser density;
   providing said vessel with baffle means extending upwardly within the volume of said vessel defining a space within said baffle means from the bottom of said vessel to the top of said vessel with means for permitting fluid flow through said baffle means from outside said baffle means to inside said baffle means only in the top zone and the bottom zone of said volume;
   providing said vessel with standpipe conduit means extending through said vessel and terminating in open communication with said medial zone within the space defined by said baffle means to thereby convey a separated liquid having greater density from said vessel to the exterior of said vessel; and
   feeding an admixture of two immiscible fluids having different densities to said vessel;
   separating said admixture into a separated liquid having lesser density and a separated liquid having greater density; and
   conveying said separated liquid having greater density through said standpipe conduit means from said vessel to the exterior of said vessel.

2. A method as recited in claim 1, further comprising:
   passing said separated liquid having greater density to the inlet of cooler means for exchanging heat energy between fluids;
   cooling said separated liquid having greater density in said cooler means; and
   mixing the thus cooled said separated liquid having greater density with a hydrocarbon feed material to produce said admixture.

3. A method as recited in claim 2, further comprising:
   withdrawing said separated liquid having lesser density through said outlet means.

* * * * *